(12) United States Patent
Nishimura et al.

(10) Patent No.: US 7,964,687 B2
(45) Date of Patent: Jun. 21, 2011

(54) OXYLAMINO GROUP-CONTAINING COMPOUND AND POLYMER

(75) Inventors: Shinichiro Nishimura, Hokkaido (JP);
Hideyuki Shimaoka, Tokyo (JP)

(73) Assignees: Sumitomo Bakelite Company, Ltd., Tokyo (JP); National University Corporation Hokkaido University, Hokkaido (JP)

( * ) Notice: Subject to any disclaimer, the term of this patent is extended or adjusted under 35 U.S.C. 154(b) by 1092 days.

(21) Appl. No.: 11/660,985

(22) PCT Filed: Jul. 7, 2005

(86) PCT No.: PCT/JP2005/012580
§ 371 (c)(1),
(2), (4) Date: Feb. 23, 2007

(87) PCT Pub. No.: WO2006/025155
PCT Pub. Date: Mar. 9, 2006

(65) Prior Publication Data
US 2008/0097061 A1  Apr. 24, 2008

(30) Foreign Application Priority Data
Aug. 31, 2004  (JP) .................. 2004-251457

(51) Int. Cl.
*C08F 120/58* (2006.01)

(52) U.S. Cl. ........ 526/304; 526/306; 526/307; 526/320; 526/323.1; 526/328; 564/123; 564/133; 564/152; 564/300; 564/301

(58) Field of Classification Search .................. 564/123, 564/133, 152, 300, 301; 526/304, 306, 307, 526/320, 323.1, 328
See application file for complete search history.

(56) References Cited

U.S. PATENT DOCUMENTS
4,666,962 A * 5/1987 Ravichandran et al. ........ 524/99
5,449,816 A    9/1995 Bauer et al.

FOREIGN PATENT DOCUMENTS
| JP | 58-069232 | 4/1983 |
| JP | 2004-264027 | 9/2004 |
| WO | WO 98/47000 | 10/1998 |
| WO | WO 2004/058687 | 7/2004 |

* cited by examiner

*Primary Examiner* — Bernard Lipman
(74) *Attorney, Agent, or Firm* — Smith, Cambrell & Russell, LLP

(57) ABSTRACT

An oxylamino group-containing compound represented by the following formula:

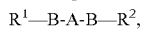

$R^1$—B-A-B—$R^2$, wherein $R^1$ represents a polymerizable group, $R^2$ represents an oxylamino group-containing group or an oxylamino derivative-containing group, B represents an ester linkage or an amide linkage, and A represents an optionally substituted alkylene group having 2 to 12 carbon atoms.

6 Claims, No Drawings

OXYLAMINO GROUP-CONTAINING COMPOUND AND POLYMER

TECHNICAL FIELD

The present invention relates to an oxylamino group-containing compound and a derivative thereof, and particularly to an oxylamino group-containing compound that specifically reacts with a sugar chain. Further, the present invention relates to a method of producing such an oxylamino group-containing compound. The present invention relates to a polymer obtained by using an oxylamino group-containing compound.

BACKGROUND ART

Sugar chain is a generic term of a molecule in which monosaccharides, such as glucose, galactose, mannose, fucose, xylose, N-acetylglucosamine, N-acetylgalactosamine, and sialic acid, and/or derivatives thereof are linked to each other via a glycoside bond to form a chain-like structure.

Sugar chains are very rich in diversity and they are substances involved in various functions that naturally-occurring organisms have. The sugar chain is often found as a complex carbohydrate, in which the sugar chain bonds to a protein, a lipid, or the like, in the body and it is one of the major constituents in the body. It has been revealed that sugar chains in the body are deeply involved in intercellular signal transduction, regulation of functions and interactions of proteins, and the like.

For example, as a biopolymer having a sugar chain, there may be mentioned cell wall proteoglycans in plant cells, which contribute to stabilization of cells; glycolipids, which influence differentiation, proliferation, adhesion, migration, and the like of cells; glycoproteins, which involve in intercellular interactions and cell recognition; and the like. There have been gradually clarified mechanisms in which these sugar chains contained in biopolymers control high-level and precise biological reactions while acting for, aiding, enhancing, adjusting, or inhibiting their functions with the biopolymers each other. Furthermore, if relationships of such sugar chains with differential proliferation of cells, cell adhesion, immunity, and cell canceration are clarified, it may be expected to make a new development by closely associating this glycoengineering with medical science, cell engineering, or organ engineering.

Patent Document 1 describes substances that specifically react with such sugar chains, and in addition, a method of separating sugar chains by using these substances and the like.

Patent Document 1: WO 2004/058687

DISCLOSURE OF THE INVENTION

The substances described in Patent Document 1 are, however, used in a form of liposome and have a problem that they generally lack stability.

Consequently, an object of the present invention is to provide an oxylamino group-containing compound for providing a sugar chain-trapping substance that specifically reacts with a sugar chain and has high stability, a polymer using this compound, and a method of producing these.

The oxylamino group-containing compound relating to the present invention is represented by formula (1) below:

(1), (wherein $R^1$ represents a polymerizable group, $R^2$ represents an oxylamino group-containing group or an oxylamino derivative-containing group, B represents an ester linkage or an amide linkage, and A represents an optionally substituted alkylene group having 2 to 12 carbon atoms).

In the oxylamino group-containing compound, $R^1$ may be a group derived from an unsaturated carboxylic acid.

In the oxylamino group-containing compound, A may represent optionally branched alkylene group having 2 to 12 carbon atoms in which —O—, —S—, or —$NR^5$— may intervene, and $R^5$ may represent a hydrogen atom or an optionally substituted alkylene group having 1 to 8 carbon atoms.

In the oxylamino group-containing compound, the oxylamino derivative-containing group represented by $R^2$ may be a group in which a protecting group for protecting an amino group bonds to an oxylamino group.

As the oxylamino group-containing compound, the compound represented by formula (2) below may be used:

(Formula 1) (2)

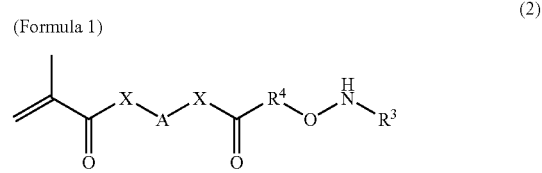

(wherein, A is as described above, $R^3$ represents a hydrogen atom or a protecting group for an amino group, $R^4$ represents an optionally substituted alkylene group having 1 to 5 carbon atoms, and X represents —NH— or —O—).

The method of producing the oxylamino group-containing compound relating to the present invention contains:

a first step in which an activated unsaturated carboxylic acid derivative, or an unsaturated carboxylic acid in the presence of a condensing agent, is reacted with a compound represented by H—X-A-X—H (wherein A represents an optionally substituted alkylene group having 2 to 12 carbon atoms and X represents —NH— or —O—); and a second step in which the product obtained in the first step is reacted with a compound represented by $R^2$—COOH (wherein $R^2$ represents an oxylamino group-containing group or its derivative-containing group).

In the method of producing the oxylamino group-containing compound, the unsaturated carboxylic acid derivative used in the first step may be selected from an acid anhydride, an acid halide, an active ester, and an active amide.

In the method of producing the oxylamino group-containing compound, A in the compound H—X-A-X—H used in the first step may represent an optionally branched alkylene group having 2 to 12 carbon atoms in which —O—, —S—, or —$NR^5$— may intervene and $R^5$ may represent a hydrogen atom or an optionally substituted alkylene group having 1 to 8 carbon atoms.

In the method of producing the oxylamino group-containing compound, $R^2$—COOH used in the second step may be a compound represented by $R^3$—NH—O—$R^4$—COOH (wherein $R^3$ represents a hydrogen atom or a protecting group for an amino group and $R^4$ represents an optionally substituted alkylene group having 1 to 5 carbon atoms).

The polymer relating to the present invention is obtained by polymerization using any of the above-described oxylamino group-containing compounds.

The polymer may be a polymer obtained by conducting the polymerization in a reaction system in which a crosslinker is further added.

The polymer may be a polymer obtained by conducting the polymerization in a reaction system further supplied with at least one kind of polymerizable compound that is neither the oxylamino group-containing compounds nor, if present, the crosslinker.

According to the present invention, there may be provided a sugar chain-trapping substance that specifically reacts with a sugar chain and has high stability.

BEST MODE FOR CARRYING OUT THE INVENTION

Hereinafter, details will be explained on the oxylamino group-containing compound, the polymer, and the method of producing these substances of the present invention.

The oxylamino group-containing compound relating to the present invention is represented by formula (1) below:

(wherein $R^1$ represents a polymerizable group, $R^2$ represents an oxylamino group-containing group or an oxylamino derivative-containing group, B represents an ester linkage or an amide linkage, and A represents an optionally substituted alkylene group having 2 to 12 carbon atoms).

$R^1$ is a polymerizable group containing a carbon-carbon double bond (C=C) and it includes, for example, a group derived from an unsaturated carboxylic acid. $R^1$ is a moiety involved in polymerization in producing the polymer of the present invention described later. $R^1$ includes, for example, $CH_2=C(CH_3)$—, $CH_2=CH$—, and the like.

B is an ester linkage or an amide linkage, and it forms, together with $R^1$, for example, $CH_2=C(CH_3)CONH$—, $CH_2=CHCONH$—, $CH_2=CHCOO$—, $CH_2=C(CH_3)COO$—, or the like.

A represents an optionally branched alkylene group having 2 to 12 carbon atoms in which —O—, —S—, or —$NR^5$— may intervene, and $R^5$ is a hydrogen atom or an optionally substituted alkylene group having 1 to 8 carbon atoms. A includes, for example, —$CH_2CH_2$—O—$CH_2CH_2$—O—$CH_2CH_2$—, —$CH_2CH_2$—S—$CH_2CH_2$—S—$CH_2CH_2$—, —$CH_2CH_2$—NH—$CH_2CH_2$—NH—$CH_2CH_2$—, —$CH_2CH_2$—O—$CH_2CH_2$—, —$CH_2CH_2$—S—$CH_2CH_2$—, —$CH_2CH_2$—, and the like.

$R^2$ represents an oxylamino group (—O—$NH_2$)-containing group or its derivative-containing group. This derivative is a group in which, as an atom or group that may bond to the nitrogen of oxylamino group, an atom or group other than hydrogen (for example, t-butoxycarbonyl group (Boc), which is a protecting group for an amino group) bonds to the nitrogen atom of amino group.

In a state where an equilibrium is established between a cyclic hemiacetal form and an acyclic aldehyde form that are derived from sugar chains in solution such as aqueous solution, the oxylamino group is reacted with the aldehyde group to form a specific and stable bond, and hence the polymer can trap the sugar chain.

Such an oxylamino group-containing compound includes, more specifically, a compound represented by formula (2) below:

(Formula 2)

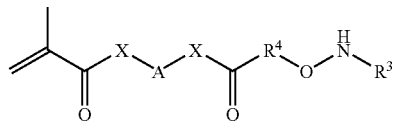

(wherein A is as described above, $R^3$ represents a hydrogen atom or a protecting group for an amino group, $R^4$ represents an optionally substituted alkylene group having 1 to 5 carbon atoms, and X represents —NH— or —O—).

Here, $R^4$ represents, similarly to A described above, an optionally branched alkylene group having 1 to 5 carbon atoms in which —O—, —S—, or —$NR^5$— may intervene, and $R^5$ is a hydrogen atom or an optionally substituted alkylene group having 1 to 8 carbon atoms. $R^4$ includes, for example, —$CH_2$—, —$CH_2CH_2$—, and the like.

In such a compound, the double bond contained in the group derived from an unsaturated carboxylic acid is used for the polymerization, while the oxylamino group is specifically reacted with the aldehyde group of a sugar chain.

An embodiment of the method of producing such an oxylamino group-containing compound contains the first step in which an activated unsaturated carboxylic acid derivative, or an unsaturated carboxylic acid in the presence of a condensing agent, is reacted with a compound represented by H—X-A-X—H (wherein A represents an optionally substituted alkylene group having 2 to 12 carbon atoms and X represents —NH— or —O—); and the second step in which the product obtained in the first step is reacted with a compound represented by $R^2$—COOH (wherein $R^2$ represents an oxylamino group-containing group or its derivative-containing group).

Here, the unsaturated carboxylic acid derivative used in the first step is a compound in which the carboxyl group of an unsaturated carboxylic acid is activated. It includes compounds in which the carboxyl group of an unsaturated carboxylic acid, such as acrylic acid, methacrylic acid, crotonic acid, maleic acid, and fumaric acid, is converted to an acid anhydride, an acid halide, an active ester, or an active amide. Specifically, it includes the compounds shown below.

(Formula 3)

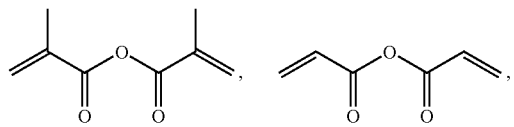

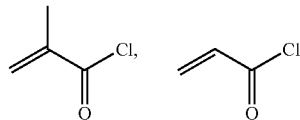

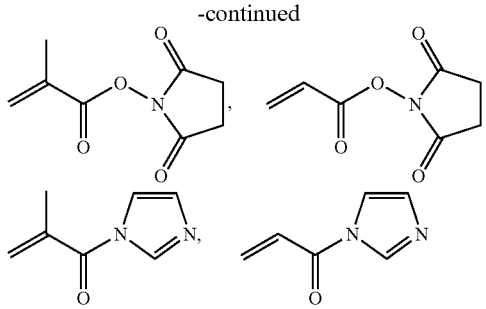

As usable unsaturated carboxylic acids used in the first step together with a condensing agent, there may be mentioned acrylic acid, methacrylic acid, crotonic acid, maleic acid, fumaric acid, and the like. As the condensing agent, there may be mentioned 1-ethyl-3-(3-dimethylaminopropyl)carbodiimide, dicyclohexylcarbodiimide (DCC), and the like.

The compound represented by H—X-A-X—H used in the first step is a compound that reacts with an unsaturated carboxylic acid or a derivative thereof. A represents an alkylene group having 2 to 12 carbon atoms, preferably 4 to 10 carbon atoms. Here, the alkylene group may be branched. Further, the alkylene group may be intervened with —O—, —S—, or —$NR^5$— in the middle of its chain. X represents —NH— or —O—. Specifically, there may be mentioned the following compounds.

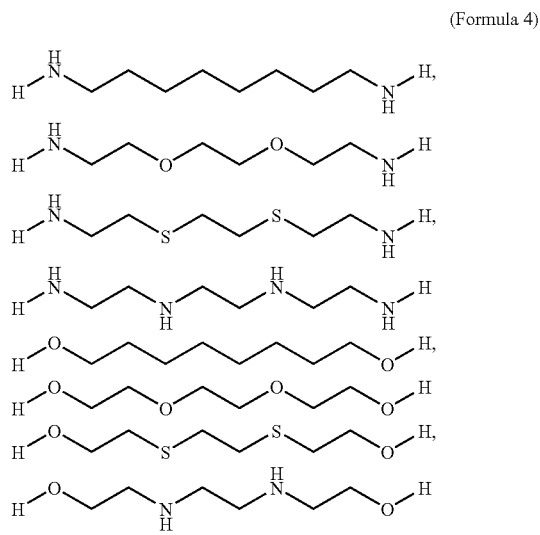

(Formula 4)

The reaction in the first step is performed at −10 to 40° C., and preferably on an ice bath. This reaction may be also performed in an atmosphere of inert gas, for example, nitrogen or argon.

The compound used in the second step is a compound represented by $R^2$—COOH (wherein $R^2$ represents an oxylamino group-containing group or its derivative-containing group as described above) Specifically, there may be mentioned $R^3$—NH—O—$R^4$—COOH (wherein $R^3$ represents a hydrogen atom or a protecting group for an amino group and $R^4$ represents an optionally substituted alkylene group having 1 to 5 carbon atoms as described above). Specifically, there may be mentioned the following compounds.

(Formula 5)

BOC—NH—O—CH₂—COOH,

BOC—NH—O—CH₂CH₂—COOH

In the second step, as the condensing agent suitably used to react the compound obtained in the first step with the compound, $R^2$—COOH, there may be mentioned a water-soluble carbodiimide, for example, 1-ethyl-3-(3-dimethylaminopropyl)carbodiimide; however, a water-insoluble carbodiimide, for example, dicyclohexylcarbodiimide (DCC) may be also used.

The reaction in the second step is performed at −10 to 40° C., and preferably on an ice bath. The reaction may be also carried out in an atmosphere of inert gas, for example, nitrogen or argon.

In both the first and second steps, the compounds obtained may be purified with column chromatography.

The polymer relating to the present invention is obtained using the oxylamino group-containing compound described above in a typical polymerization, for example, suspension polymerization. This polymerization may be performed in the presence of a multifunctional compound as a crosslinker to polymerize the oxylamino group-containing compound.

Such a compound includes, for example, (1) di(meth)acrylates or tri(meth)acrylates of polyols, for example, such compounds in which the polyol is ethylene glycol, propylene glycol, trimethylolpropane, glycerin, polyoxyethylene glycol, polyoxypropylene glycol, polyglycerin, or the like, (2) compounds (I) in which the unsaturated acid is other than (meth) acrylic acid, for example, maleic acid, fumaric acid, or the like, (3) bisacrylamides, for example, N,N'-methylenebisacrylamide and the like, (4) di(meth)acrylates or tri(meth) acrylates obtained by reacting a polyepoxide and (meth) acrylic acid, (5) di(meth)acrylic carbamoylesters obtained by reacting a polyisocyanate with a (meth)acrylic hydroxyester, for example, such compounds in which the polyisocyanate is tolylene diisocyanate or hexamethylene diisocyanate, and (6) polyallylated compounds, for example, allylated starch, allylated cellulose, diallyl phthalate, tetraallyloxyethane, pentaerythritol triallyl ether, trimethylolpropane triallyl ether, diethylene glycol diallyl ether, triallyl trimellitate, and the like. Among these, in the present invention, preferred are ethylene glycol di(meth)acrylate, propylene glycol di(meth) acrylate, N,N'-methylenebis(meth)acrylamide, and the like.

That is, the polymer relating to the present invention has the following structure:

-(a moiety of a oxylamino group-containing compound)$_m$-(a crosslinker moiety)$_n$-

Particularly, when the compound of formula (2) is used as the oxylamino group-containing compound and ethylene glycol dimethacrylate as the crosslinker, the polymer is represented by the following formula:

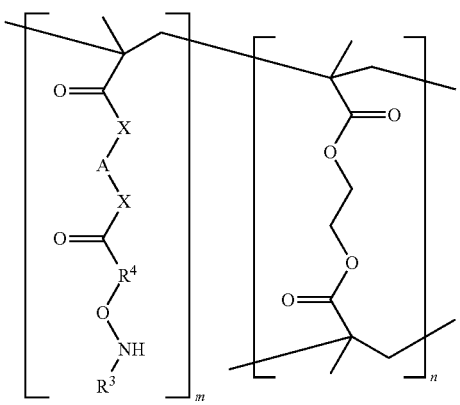

(Formula 6)

In any of these formulae, the polymer is represented as though it is a block copolymer, in which the moiety derived from each of the monomer components, that is, the oxylamino group-containing compound and the crosslinker, forms each block. However, the polymer may be a polymer in which each monomer is randomly polymerized.

This polymer may further contain, in addition to moieties derived from the oxylamino group-containing compound or the crosslinker, moieties derived from other polymerizable compounds. Such compounds include acrylic acid and its derivative, methacrylic acid and its derivative, and the like. The oxylamino group content and other predetermined physical properties of the polymer may be controlled by containing such a compound as a monomer.

For the melting point of such a polymer, the upper limit is 250° C., and preferably 100° C., while the lower limit is 0° C., and preferably 20° C. For the glass transition point, if observed, the upper limit is 250° C., and preferably 100° C., while the lower limit is −20° C., and preferably 0° C. In the polymer having a melting point and, if any, a glass transition point in such ranges, its molecular chain possesses high mobility at 0 to 100° C., that is, temperatures in handling an aqueous solution. Typically, sugar chains are dissolved in water or an aqueous buffer solution in many cases, and hence the reaction of the polymer and the sugar chain is performed at 0 to 100° C., typically at room temperature to 90° C. For this reason, the polymers with the melting point and glass transition point as described above, because of flexibility of their molecular chains, exhibit high wettability (affinity) with sugar chain solutions and high reactivity in reacting with the sugar chain.

When the polymer is formed into particles, the particle shape is preferably spherical. For the particle size, the upper limit is 200 μm, and preferably 150 μm; the lower limit is 20 μm, and preferably 50 μm; and the average particle size is 80 to 100 μm. The polymer particles having a particle size in this range are readily collected by centrifugation, filtration or the like, and are considered to react with a sugar chain in high efficiency since they have sufficient surface area. If the particle size is significantly larger than the above range, the efficiency of reaction with a sugar chain may be lowered because of a decrease in surface area. If the particle size is significantly smaller than the above range, the particles may be hard to be collected, particularly with a filter. Moreover, when the particles are used while packed into a column, too small particle size may increase the pressure loss in passing a solution through the column.

Such polymers may be obtained as follows: the oxylamino group-containing compound and the crosslinker are dissolved in a solvent such as chloroform; subsequently, in the case of suspension polymerization, the solution is dispersed in a dispersion medium, such as water, using a dispersion stabilizer for stabilizing droplets of the starting materials; and a polymerization initiator is added to the reaction system to perform polymerization. The polymer thus obtained may be collected by a technique such as centrifugation.

When a protecting group bonds to the oxylamino group, the protecting group may be removed by a typical deprotection reaction, for example, by treating with trifluoroacetic acid (TFA). The polymer thus obtained may be stored in an aqueous dispersion form because it is stable in water.

The polymers thus obtained can trap a sugar chain because the oxylamino group moiety therein specifically reacts with the sugar chain. Therefore, the polymers may be used for isolating a sugar chain component in a biopolymer. For example, by performing sugar chain-trapping reaction in such a way that the polymer is formed into particles, and the particles are packed into a column, flow channel, or the like, through which a sample is flowed or in such a way that the polymer is directly put into a sample solution, the sugar chain can be isolated from this sample. Furthermore, when the polymer is formed into particles, the particles are stable in an aqueous dispersion and easily collected by centrifugation or the like, making the polymer handling more convenient compared to the conventional case where the polymer is used in a form of liposome.

EXAMPLES

Hereinafter, the present invention is explained with reference to Examples. However, the present invention is not limited to these Examples.

Example 1

Synthesis of Monomer

Compound (b), which is an oxylamino group-containing compound, was synthesized according to the following scheme.

(Formula 7)

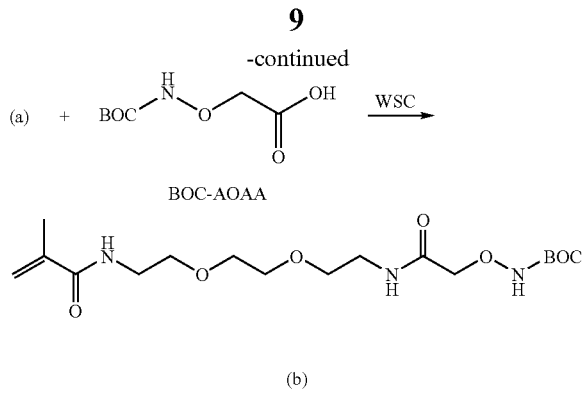

(A) Synthesis of Compound (a)

A solution prepared by dissolving 5 g (0.03 mol) of methacrylic anhydride (MAH) in 100 ml of chloroform was added dropwise, on an ice bath, to a solution prepared by dissolving 25 g (0.17 mol) of (ethylenedioxy)bis(ethylamine) (EDBEA) in 100 ml of chloroform. The reaction vessel was filled with nitrogen and the content was stirred overnight. The solvent was evaporated from the resultant reaction solution, and the residue was chromatographed on a silica gel column (eluent: mixed solvent of 90 vol % chloroform and 10 vol % methanol) to collect a desired fraction. The solvent was evaporated from the fraction to obtain compound (a) (Yield: 5.0 g, 71%).

(B) Synthesis of Compound (b)

To a solution prepared by dissolving 5 g (0.023 mol) of compound (a) in 100 ml of chloroform, were added 1.5 equivalents of Boc-aminooxyacetic acid (BOC-AOAA) and 1.5 equivalents of a water-soluble carbodiimide compound (WSC), 1-ethyl-3-(3-dimethylaminopropyl)carbodiimide. The reaction vessel was sealed tightly and filled with nitrogen, and the content was stirred overnight. The solvent was evaporated from the resultant reaction solution, and the residue was chromatographed on a silica gel column (eluent: mixed solvent of 90 vol % chloroform and 10 vol % methanol) to collect a desired fraction. The solvent was evaporated from the fraction to obtain compound (b) (Yield: 4.6 g, 50%).

The resultant substance was confirmed to be compound (b) by NMR and Matrix Assisted Laser Desorption Ionization-Time Of Flight-Mass Spectrometry (MALDI-TOF-MS).

(Synthesis of Polymer)

A three-necked flask was charged with 25 ml of 5% aqueous solution of polyvinyl alcohol (PVA) and purged with nitrogen. To the three-necked flask was introduced a mixture composed of 1 g (2.6 mmol) of compound (b), ethylene glycol dimethacrylate (EGDMA: 5 mol %), and 1 ml of chloroform. The reaction system was stirred while the temperature was maintained at 60° C. to disperse compound (b) and EGDMA, which were monomers contained in the mixture, in the aqueous PVA solution. Subsequently, to start polymerization, azobisisobutyronitrile (AIBN) was added as a polymerization initiator in an amount of 3% by weight with respect to compound (b). After performing reaction at 60° C. for 16 hours, the resultant polymer particles were collected by centrifugation and washed with methanol and water.

After washing, to the polymer particles were added 20 ml of methanol and 10 ml of trifluoroacetic acid (TFA), and the mixture was shaken at 40° C. for 16 hours to perform deprotection of the BOC group used as a protecting group. The resultant polymer particles were collected by centrifugation and washed with methanol and water. The resultant polymer particles were able to be stored after dispersed in an appropriate quantity of water.

The particle size distribution of the polymer obtained here ranged from 20 to 200 μm with an average particle size of 80 μm. When measured with differential scanning calorimetry (DSC), the melting point was 50.9° C. and no glass transition point was observed.

The invention claimed is:

1. An oxylamino group-containing compound represented by formula (1) below:

$$R^1\text{—B-A-B—}R^2 \tag{1}$$

wherein $R^1$ represents a polymerizable group, $R^2$ represents an oxylamino group-containing group or an oxylamino derivative-containing group, B represents an ester linkage or an amide linkage, and A represents an optionally substituted alkylene group having 2 to 12 carbon atoms, wherein said oxylamino group-containing compound is represented by formula (2) below:

(2)

(Formula 1)

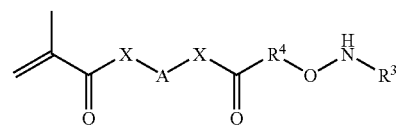

wherein A is as described above, $R^3$ represents a hydrogen atom or an protecting group for an amino group, $R^4$ represents an optionally substituted alkylene group having 1 to 5 carbon atoms, and X represents —NH— or —O—.

2. The oxylamino group-containing compound according to claim 1, wherein A represents an optionally branched alkylene group having 2 to 12 carbon atoms in which —O—, —S—, or —N—$R^5$— may intervene, and $R^5$ represents a hydrogen atom or an optionally substituted alkylene group having 1 to 8 carbon atoms.

3. A polymer obtained by polymerization of the oxylamino group-containing compound according to any of claim 1.

4. The polymer according to claim 3, wherein said polymerization is suspension polymerization.

5. The polymer according to claim 3, wherein said polymer is obtained by performing said polymerization in a reaction system further supplied with a crosslinker.

6. The polymer according to claim 3, wherein said polymer is obtained by performing said polymerization in a reaction system further supplied with at least one kind of polymerizable compound that is neither said oxylamino group-containing compound nor, if present, said crosslinker.

* * * * *